(12) United States Patent
Sullivan

(10) Patent No.: US 10,244,941 B2
(45) Date of Patent: Apr. 2, 2019

(54) SURGICAL GUIDE AND SURGICAL METHOD

(71) Applicant: L & L Sullivan PTY LTD, Balwyn, Victoria (AU)

(72) Inventor: Laurence John Sullivan, Balwyn (AU)

(73) Assignee: L & L SULLIVAN PTY LTD. (AU)

( * ) Notice: Subject to any disclaimer, the term of this patent is extended or adjusted under 35 U.S.C. 154(b) by 276 days.

(21) Appl. No.: 14/440,828

(22) PCT Filed: Nov. 4, 2013

(86) PCT No.: PCT/AU2013/001272
§ 371 (c)(1),
(2) Date: May 5, 2015

(87) PCT Pub. No.: WO2014/066954
PCT Pub. Date: May 8, 2014

(65) Prior Publication Data
US 2015/0282706 A1   Oct. 8, 2015

(30) Foreign Application Priority Data
Nov. 5, 2012   (AU) ................................ 2012904830

(51) Int. Cl.
| | |
|---|---|
| *A61B 3/125* | (2006.01) |
| *A61F 9/008* | (2006.01) |
| *A61B 90/00* | (2016.01) |
| *A61F 9/007* | (2006.01) |
| *G02C 7/04* | (2006.01) |
| *G02C 7/02* | (2006.01) |

(52) U.S. Cl.
CPC .............. *A61B 3/125* (2013.01); *A61B 90/39* (2016.02); *A61F 9/008* (2013.01); *A61B 2090/3937* (2016.02); *A61F 9/007* (2013.01); *G02C 7/021* (2013.01); *G02C 7/04* (2013.01)

(58) Field of Classification Search
CPC ......... A61B 3/125; A61B 19/54; A61F 9/008; A61F 9/007
USPC .......................................................... 606/4
See application file for complete search history.

(56) References Cited

U.S. PATENT DOCUMENTS

| | | | |
|---|---|---|---|
| 4,406,285 A | * | 9/1983 | Villasenor ............... A61F 9/013 33/1 B |
| 4,520,815 A | | 6/1985 | Marinoff |

(Continued)

FOREIGN PATENT DOCUMENTS

WO          1995023556 A1    9/1995

*Primary Examiner* — Amanda K Hulbert
*Assistant Examiner* — Roland Dinga
(74) *Attorney, Agent, or Firm* — Tarolli, Sundheim, Covell & Tummino LLP

(57) ABSTRACT

A surgical guide comprising a contact lens comprising a body on which is disposed a reticule, the reticule may be used to guide a surgeon operating on an eye on which the contact lens is located is disclosed. Also disclosed is a surgical method, the method comprising using a reticule on a contact lens to guide a surgical procedure performed on an eye to thereby perform the surgical method. The reticule may comprise one or more concentric circle or concentric shape and/or a set of lines. The reticule may also comprise one or more meridian and/or one or more parallel. The reticule may further comprise one or more net or grid.

23 Claims, 7 Drawing Sheets

(56) References Cited

U.S. PATENT DOCUMENTS

| | | | | |
|---|---|---|---|---|
| 4,688,570 A | * | 8/1987 | Kramer | .................. A61F 9/013 606/166 |
| 4,880,017 A | | 11/1989 | Soli et al. | |
| 2002/0123744 A1 | * | 9/2002 | Reynard | ............. A61F 9/00736 606/6 |
| 2009/0024023 A1 | * | 1/2009 | Welches | ............... A61B 18/201 600/424 |

* cited by examiner

SURGICAL GUIDE AND SURGICAL METHOD

FIELD

THIS INVENTION described herein relates generally to a surgical guide and a surgical method. In particular, the invention is directed to a surgical guide comprising a reticule and a surgical method in which the surgical guide comprising the reticule is used, although the scope of the invention is not necessarily limited thereto.

BACKGROUND

Ophthalmic treatment, including laser surgery, performs treatment on different surfaces of the eye and requires accurate positioning. To do this, the location of the target area for surgery needs to be known.

To assist in this orientation, surgical guidance systems are routinely used in ophthalmic surgery to guide the surgical process. Existing systems make use of complex computer models, registering and tracking the position of a person's eye with video, range determining systems and generating images of an internal structure of an eye.

These complex systems are not readily available to all.

SUMMARY

The present invention is broadly directed to a surgical guide comprising a reticule and a surgical method in which the surgical guide utilises the reticule. Advantageously, the present invention does not require any complex or expensive equipment to accurately orient position relative to a patient's eye. A preferred advantage of the surgical guide and surgical method is that there is a reduced or no parallax error.

In one aspect, there is provided a surgical guide comprising:

a contact lens comprising a body on which is disposed a reticule, whereby the reticule is used to guide a surgeon operating on an eye on which the contact lens is located.

In another aspect, there is provided a surgical method, the method comprising:

using a reticule on a contact lens to guide a surgical procedure performed on an eye to thereby perform the surgical method.

According to the method of the invention The reticule and/or any part of reticule 120 may be used as a guide.

The method may further include the step of placing the contact lens onto the eye.

The method may further include cutting through the contact lens at an area indicated by the reticule to access a corresponding area of the eye.

The method may further include removing the contact lens.

According to either the first or second embodiment, the reticule may be comprised on a surface of the contact lens. The surface may be an inner surface or an outer surface.

According to either the first or second embodiment, the reticule may comprise a set of lines.

The reticule may be used in orientation and identification of a particular location.

According to either the first or second embodiment, the reticule may comprise one or more meridians. The one or more meridians may comprise a plurality of meridians.

The plurality of meridians may be spaced regularly or irregularly.

Two or more meridians may be clustered around, at or near a region of interest.

The plurality of meridians may comprise one or more of major full-length meridians, one or more minor full-length meridians, one or more major partial-length meridians and one or more minor partial length meridians.

According to either the first or second embodiment, the reticule may comprise one or more parallels. The one or more parallels may comprise a plurality of parallels.

The plurality of parallels may be spaced regularly or irregularly.

Two or more parallels may be clustered around, at or near a region of interest.

The plurality of parallels may comprise one or more major full-length parallels, one or more minor full-length parallels, one or more major-partial length meridians and one or more minor partial length meridians.

The meridians and parallels may comprise an identical thickness or may have different thicknesses.

According to either the first or second embodiment, the reticule may comprise one or more nets or grids.

The one or more nets or grids may comprise a plurality of circles, squares, rectangles, triangles, pentagons, hexagons or any other shape.

The shape of the one or more nets or grids may comprise a regular shape or an irregular shape.

According to either the first or second embodiment, the reticule may comprise one or more crosshairs.

According to either the first or second embodiment, the reticule may comprise one or more duplex cross-hairs, wherein one or more bars of a respective duplex cross-hair of the one or more duplex cross-hair is thick on the perimeter and thins out in the middle or in an area of interest.

According to either the first or second embodiment, the reticule may comprise two or more concentric circles or concentric shapes.

According to either the first or second embodiment, the reticule may comprise two or more eccentric circles or eccentric shapes.

According to either the first or second embodiment, the reticule centre may or may not correspond with the contact lens centre.

According to either the first or second embodiment, the reticule may comprise one or more spokes radiating from a centre of the contact lens.

Each of the one or more spokes may follow the curve of the contact lens from centre to outer perimeter.

According to either the first or second embodiment, the reticule may comprise solid and/or broken lines.

According to either the first or second embodiment, the reticule may comprise dots or dashes.

According to either the first or second embodiment, the reticule may comprise one or more regions of different scale.

According to either the first or second embodiment, the reticule may further comprise one or more tick marks.

According to either the first or second embodiment, the reticule may comprise one or more stadia marks.

According to either the first or second embodiment, the reticule may comprise one or more numerical indicators.

According to either the first or second embodiment, the reticule may comprise one or more stadia marks and one or more numerical indicators.

According to either the first or second embodiment, one or more region of the contact lens may comprise one or more indicators.

According to either the first or second embodiment, the reticule may be customised to an individual eye, wherein the customised reticule allows ready location of one or more target area in the individual eye.

The invention also provides a guide and method substantially as herein described with or without reference to the Figures.

Any discussion of the prior art throughout the specification should in no way be considered as an admission that such prior art is widely known or forms part of the common general knowledge in the field.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS

In order that the present invention may be readily understood and put into practical effect, reference will now be made to the accompanying illustrations, wherein like reference numerals refer to like features and wherein:

FIGS. 3-6 show a perspective, side and plan view of another embodiment of a surgical guide according to the invention.

DETAILED DESCRIPTION

The inventor has produced a surgical guide comprising a reticule and a surgical method in which the surgical guide comprising the reticule is used, although the scope of the invention is not necessarily limited thereto.

During ophthalmic surgery, including laser surgery, movement of the eye will occur. This can be due to voluntary or involuntary movement of the eye and head motion. Surprisingly, as exemplified here, the present inventor has provided a novel and inventive device and method for overcoming the difficulties associated with eye movement during ophthalmic surgery. Advantageously, the present invention does not require the comparatively complex equipment and large, capital expenditure required by conventional systems.

An additional advantage is that in a preferred embodiment, parallax error is reduced or even eliminated.

As used herein, a reticule is any set of lines. Such a set of lines may also be referred to as a graticule. In the present invention, the reticule finds application in orientation and identification of a particular location.

Figure 1:
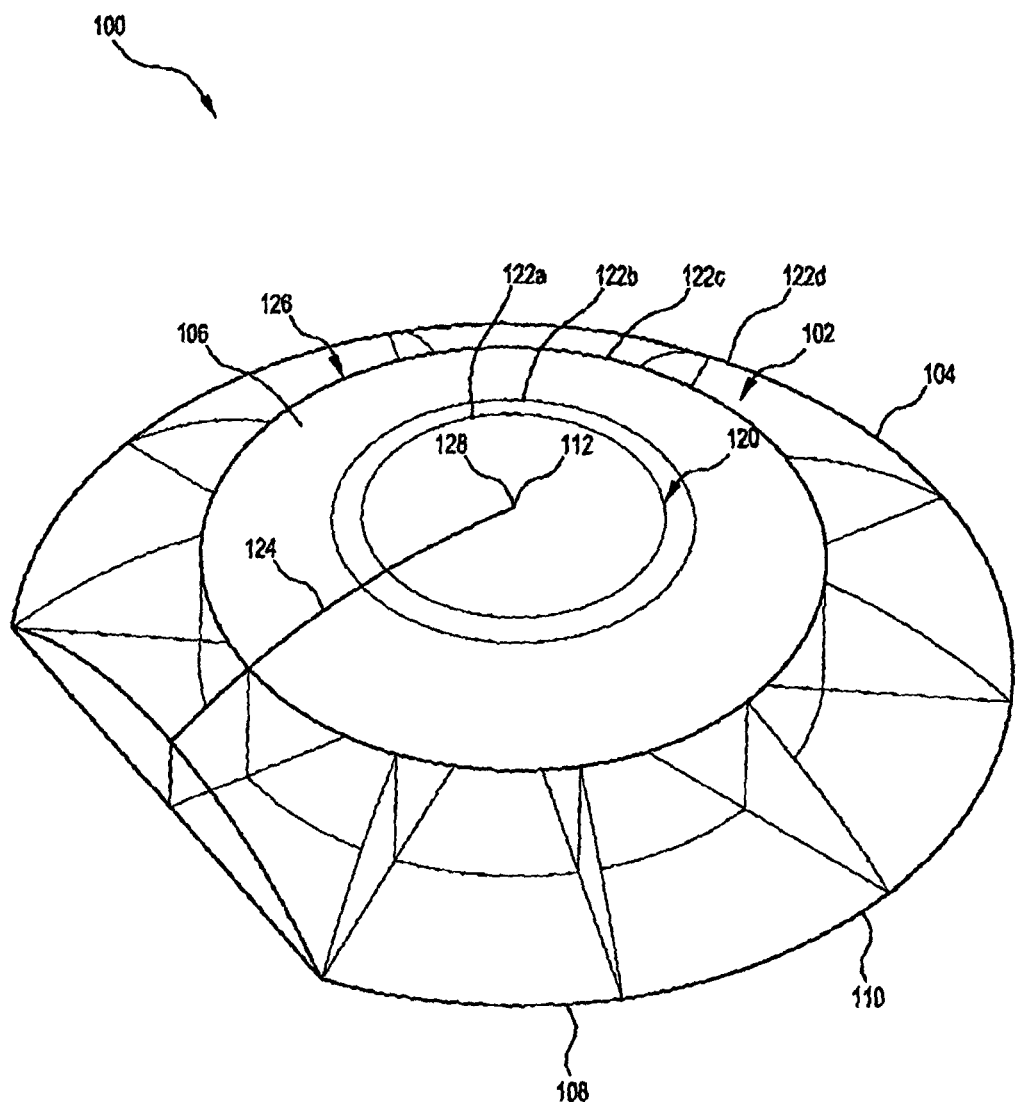
FIG. 1 shows a top perspective view of one embodiment of a surgical guide according to the invention.
Figure 2:
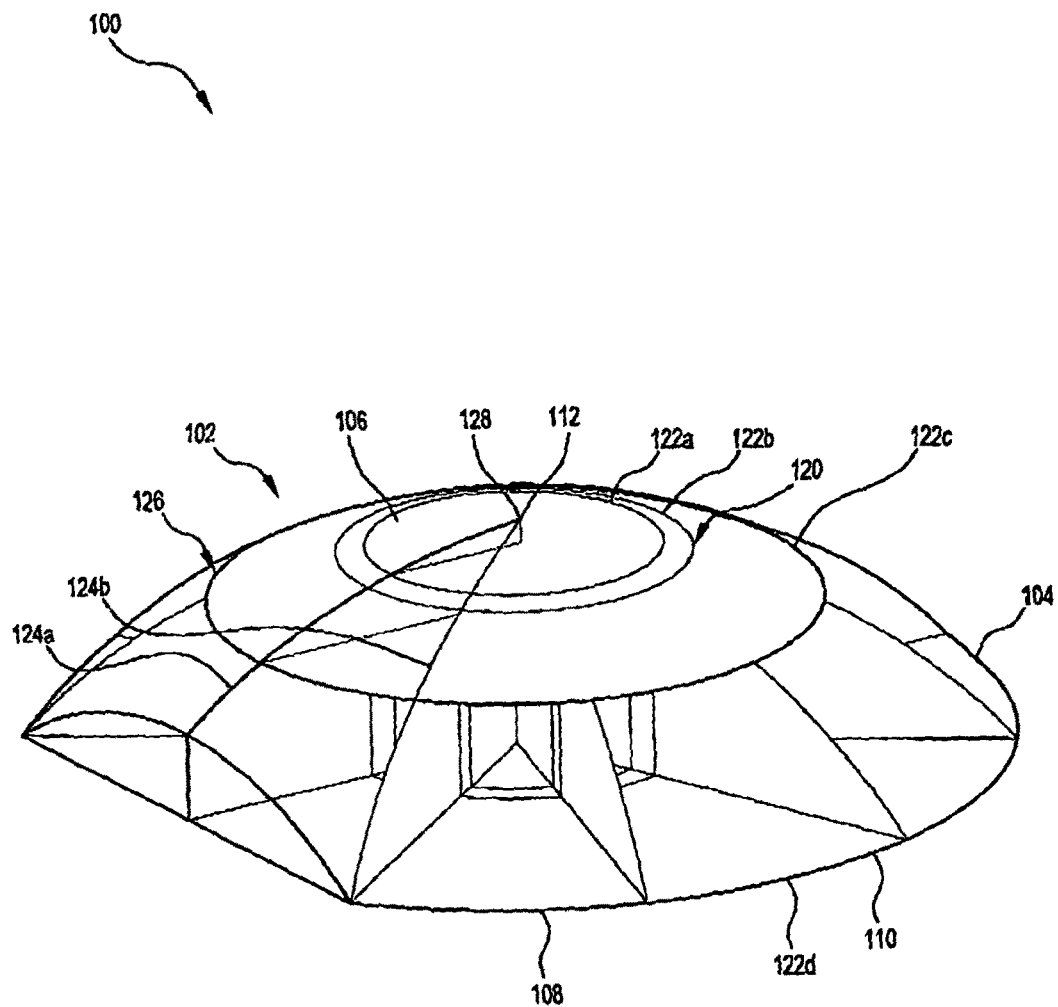
FIG. 2 shows a side perspective view of one embodiment of a surgical guide according to the invention.

FIGS. 1 and 2 show one embodiment of a surgical guide 100 according to the invention. Guide 100 comprises a contact lens 102 comprising a body 104 on which is disposed a reticule 120.

The lines that are not labelled in FIGS. 1 and 2 do not form part of reticule 120 and are merely included as an aid to show depth in a three-dimensional type view. These non-reticule lines or depth-indicating lines are thinner than the lines which form reticule 120.

The contact lens 102 comprises a centre 112, an outer perimeter 110, an external surface 106 and an inner surface 108. In position on an eye, the inner surface 108 contacts the eye, while the external surface 106 is exposed.

Reticule 120 may be used by a surgeon as a guide or grid while operating on an eye on which the contact lens 102 is located.

In the embodiment shown in FIGS. 1 and 2, reticule 120 comprises a plurality or a series of parallels 122 and a plurality or a series of meridians 124. Parallels 122 and meridians 124 make up a set of lines 126. In this way, the set of lines 126 may comprise a net or grid.

Parallels 122 comprise a plurality or series of concentric circles about the reticule centre 128, which in this embodiment is located at the contact lens centre 112.

In other embodiments, the reticule centre 128 does not correspond with the contact lens centre 112.

In still other embodiments, parallels 122 are eccentric circles, i.e. non-concentric circles which do not have the same centre.

In the embodiment of FIGS. 1 and 2, parallels 122 are positioned with an increasing radius or size as shown by parallels 122a, 122b, 122c and 122d.

Parallel 122d is co-terminus with and marks the outer edge or contact lens outer perimeter 110.

In the embodiment shown in FIGS. 1 and 2, parallels 122a, 122b, 122c, 122d are spaced or positioned at irregular intervals. In other embodiments, parallels 122 are spaced or positioned at regular intervals. From the teaching herein, a skilled person is readily able to select alternate arrangements for parallels 122. For example, two or more parallels 122 may be clustered together around, at or near a region of interest.

The guide 122 in FIGS. 1 and 2 is shown to comprise four parallels, 122a, 122b, 122c, 122d. In other embodiments, guide 100 may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more parallels 122.

Meridians 124 radiate from the reticule centre 128 and intersect on the various parallels 122 at different points, as shown by meridians 124a and 124b in FIG. 2. For ease of visualisation, only one meridian 124a is shown in FIG. 1 and only two meridians 124a, 124b are shown in FIG. 2. In one embodiment, meridians 124 radiate from the reticule centre 128 at regular intervals. For example, meridians 124 may be spaced or positioned at every 30° on guide 100. In other embodiments, meridians 124 may be spaced or positioned to radiate at every 5, 10, 15, 20, 25, 35, 40, 45, 50, 55, 60, 65, 70, 75, 80, 85, 90, 95, 100, 105, 110, 115, 120, 125, 130, 135, 140, 145, 150, 155, 160, 165, 170, 175 or 180°.

From the teaching herein, a skilled person is readily able to select alternate numbers and arrangements for the one or more meridian 124. For example, one or more meridians 124 may be spaced or positioned at irregular angular intervals on guide 100. Guide 100 may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more meridians 124.

In other embodiments, two or more meridians 124 may be clustered together around, at or near a region of interest.

In a preferred embodiment, reticule 129 is comprised on a surface 108, 110 of contact lens 102. The surface may be the inner surface 108 and/or the outer surface 110 of lens 102.

FIGS. 1 and 2 show an embodiment in which reticule 120 comprises a grid made up of circular parallels 122 and curvilinear meridians 124. In other embodiments, reticule 120 comprises a grid comprising parallels 122 comprising a plurality of squares, rectangles, triangles, pentagons, hexagons or any other shape including regular and irregular shapes and linear or curvilinear meridians 124. A regular shape is one which is equiangular, i.e. all angles are equal in measure, and equilateral, i.e. all sides have the same length. An irregular shape is one that is not a regular shape. The skilled person understands that parallels 120 and meridians 124 will comprise a shape suitable to achieve the desired reticule 120 shape. The plurality of squares, rectangles, triangles, pentagons, hexagons or any other shape making up the grid may be concentric or eccentric.

Figure 3:
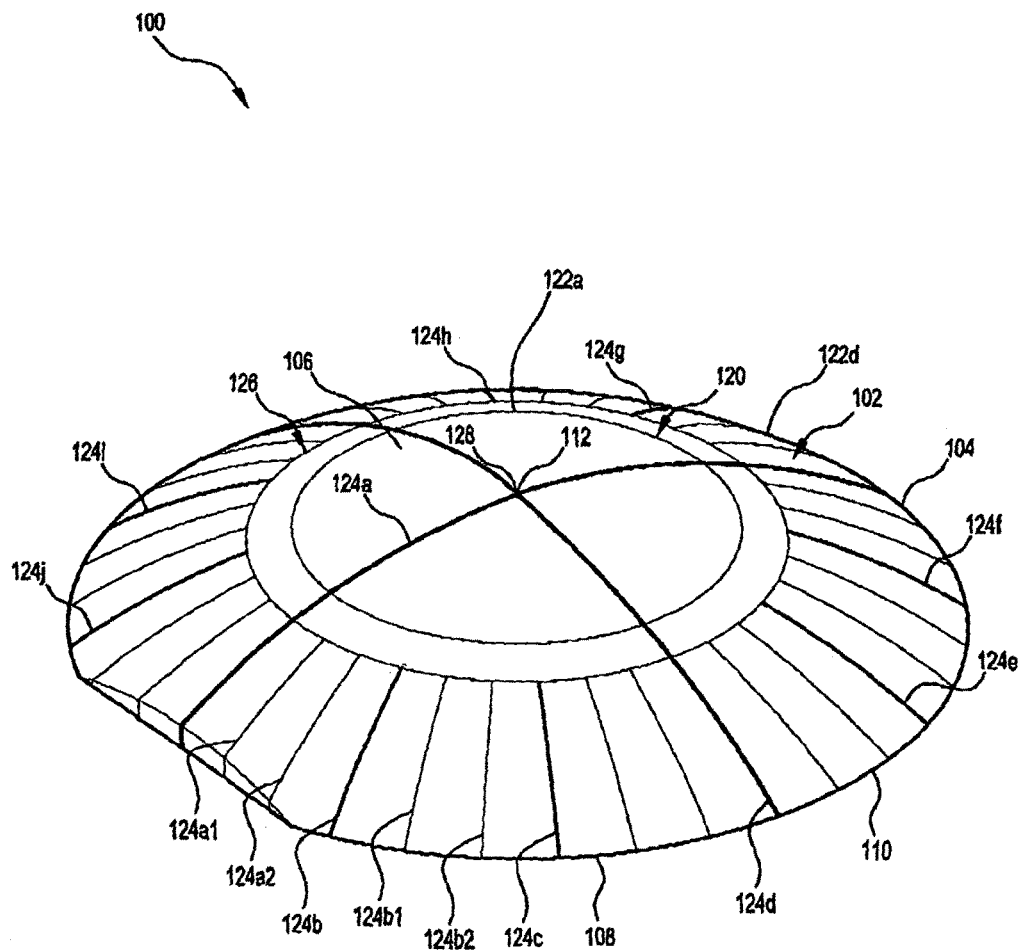
Figure 4:
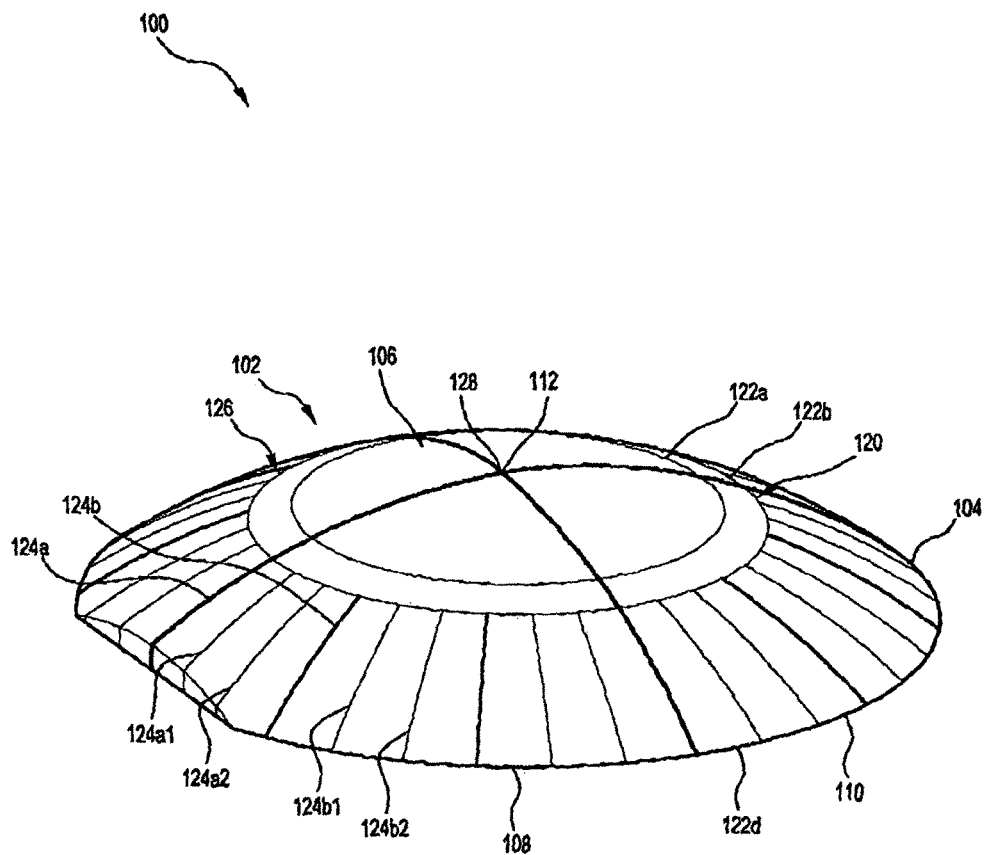
Figure 5:
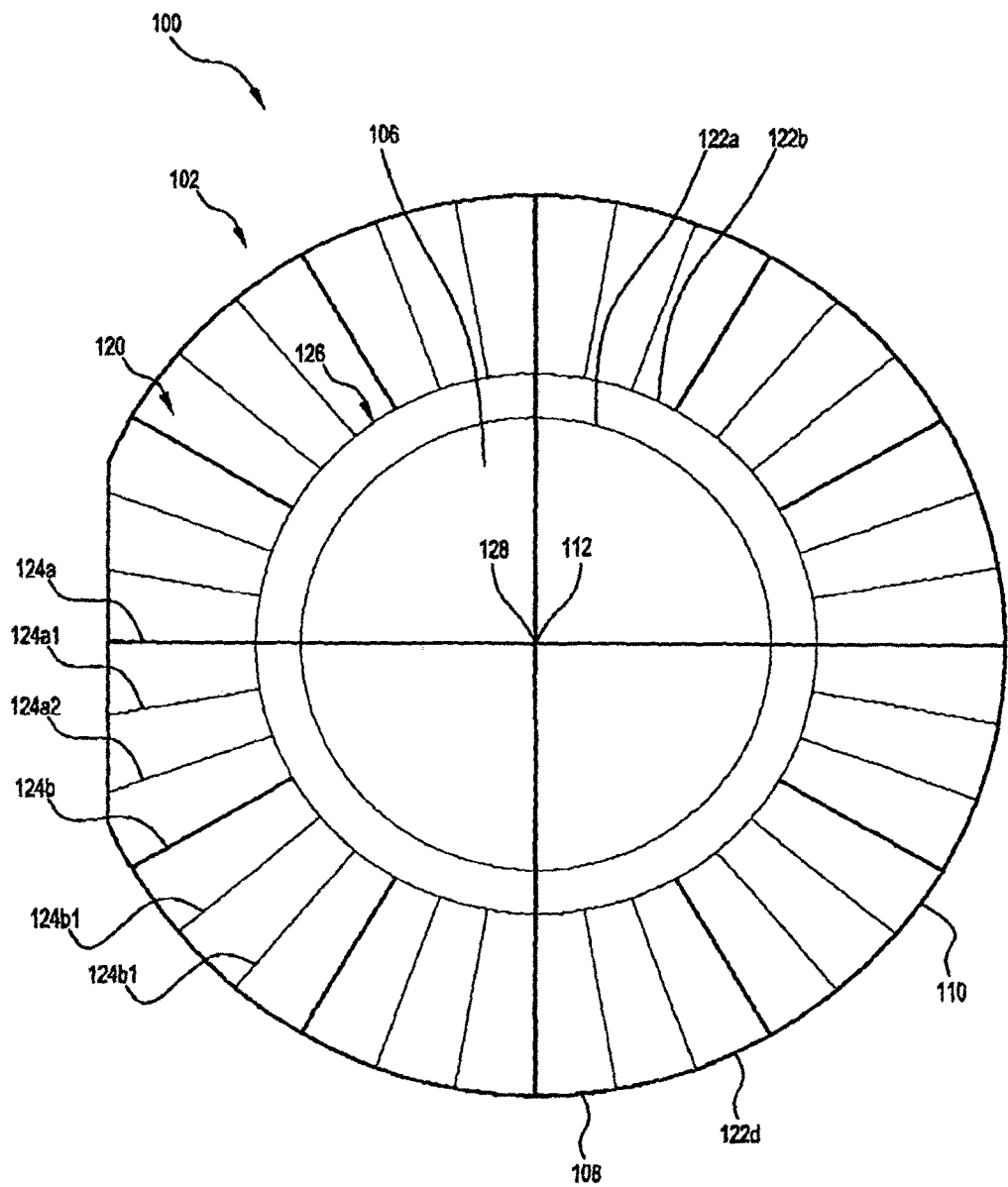
Figure 6A:
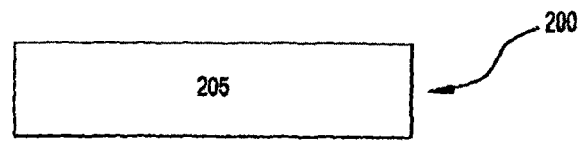
FIGS. 6A-D show flow charts showing various embodiment of a method according to the invention.
Figure 6B:
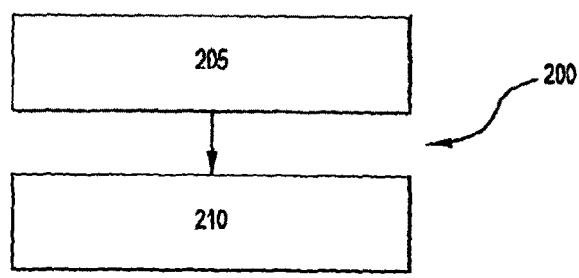
Figure 6C:
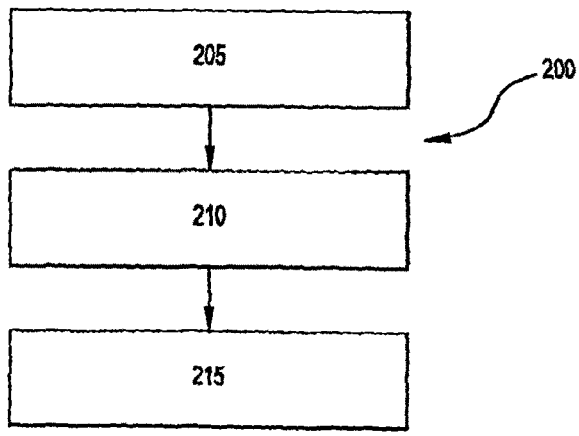
Figure 6D:
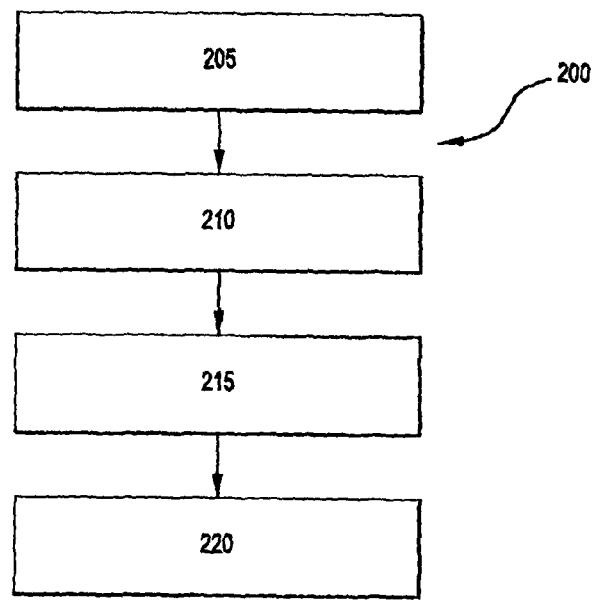

FIGS. 3-5 show a perspective, side and plan view, respectively, of another embodiment of surgical guide 100. Unlike FIGS. 1 and 2, FIGS. 3-5 do not include any non-reticule lines.

In the embodiment shown in FIGS. 3-5, only three parallels 122a, 122b and 122d are shown. Like the embodiments shown in FIGS. 1 and 2, parallel 122d in the embodiment shown in FIGS. 3-5 is co-terminus with and marks the outer edge or contact lens outer perimeter 110. Parallel 122c has been omitted because in this application sufficient guidance is provided by parallels 122a, 122b, 122d.

The embodiment of FIGS. 3-5 comprises additional meridians 124 than are utilised in the embodiments of FIGS. 1 and 2. Two full-length meridians 124a, 124d are comprised which span the full-length of guide 100, from a first point on the outer perimeter 110 through the centre 112 to an opposite second point on the opposite side and outer perimeter 110.

For ease of identification and orientation, full-length meridians 124a, 124d are thicker than the other meridians 124.

Eight major partial-length meridians 124b, 124c, 124e, 124f, 124g, 124h, 124i, 124j are also comprised in the embodiment of FIGS. 3-5. Major partial-length meridians 124b, 124c, 124e, 124f, 124g, 124h, 124i, 124j, span part of the length of guide 100, from parallel 122b to parallel 122d.

In the embodiment shown in FIGS. 3-5, between each full-length meridian and each major partial-length meridian are located minor partial-length meridians. Two minor partial-length meridians are shown between each of the full-length meridians and major partial-length meridians. So as not to overload FIGS. 3-5 with labels, only minor-partial-length meridians 124a1, 124a2 between full-length meridian 124a and partial-length meridian 124b and minor-partial-length meridians 124b 1, 124b2 between partial-length meridian 124b and partial-length meridian 124c are labelled.

The minor partial-length meridians 124a1, 124a2, 124b1, 124b2, and the non-labelled minor-partial-length meridians, are shown in thinner lines than the other meridians 124 and parallels 122.

The embodiment of FIGS. 3-S shows two minor partial length meridians between each full-length meridian or major-partial-length meridian. In other embodiments other numbers of minor partial length meridians are comprised, for example, 3, 4, 5, 6, 7, 8, 9 or 10.

Again for ease of identification and orientation, major partial-length meridians 124b, 124c, 124e, 124f, 124g, 124h, 124i, 124j are the same thickness as full-length meridians 124a, 124d, while minor partial-length meridians 124a1, 124a2, 124b1, 124b2 and the other non-labelled minor partial-length meridians are shown to be thinner. The use of lines of different thicknesses is of significant advantage because it allows ready orientation and identification and also allows the judgement of distance or size.

The inventor has included the additional meridians 124, i.e. full-length meridians and major and minor partial-length meridians, in the embodiment of FIGS. 3-5 to provide additional guidance in the outer region of surgical guide 100. This shows how surgical guide 100 may be customised to suit the particular surgical application or even an individual eye by changing the set of lines 126 which comprise reticule 120.

In another embodiment additional parallels 122, including full-length and major and minor partial-length parallels, may be comprised in reticule 120.

In still other embodiments, reticule 120 may comprise one or more crosshairs. Such cross-hairs may comprise a duplex cross-hair. In a duplex cross-hair, one or more bars of the cross-hair is thick on the perimeter and thins out in the middle or in an area of interest.

Reticules 120 of FIGS. 1-5 comprises solid lines. In other embodiments, the reticule 120 may comprise broken lines, dashes and/or dots. Any of one or more of parallels and/or one or more of meridians, including full-length, major and minor partial length meridians and parallels, may comprise broken lines, dashes and/or dots in whole or in part.

In one embodiment, reticule 120 may comprise one or more region of different scale.

In another embodiment, reticule 120 may further comprise one or more tick marks. The one or more tick marks may be comprised on one or more lines comprising the set of lines 126, such as, on one or more parallel and/or one or more meridian, including full-length, major and minor partial length meridians and parallels.

In another embodiment, reticule 120 may comprise one or more stadia marks. The stadia mark may be useful to the surgeon to measure or estimate distance. Each of the one or more stadia marks may comprise a notch or similar indication.

Each stadia mark may also be identified with a numerical value.

In still another embodiment, one or more region of the contact lens 100 may comprise one or more indicator. The region comprising the one or more indicator may be bounded by the reticule or not. The indicator may be a shading, colouring or any other suitable indication to identify an area. The indicator may communicate to the surgeon an area for particular attention or an area to be ignored.

In a particular embodiment, the reticle 120 may be customised to an individual eye. That is, the reticule may be designed to allow ready location of one or more target area in the individual cyc. For example, two regions of interest may be readily identified by the reticule comprising two customised cross-hairs, one surrounding each of the areas of interest.

The invention also provides a surgical method. One embodiment of the method of the invention is shown in FIG. 3A. Method 200 comprises the step 205 of using the reticule 120 on the contact lens 102 to guide a surgical procedure performed on an eye. The reticule 120 and/or any part of reticule 120 may be used as a guide.

Method 200 may further comprise step 210 placing the contact lens 100 onto the eye.

The method 200 may further comprise step 215 cutting through the contact lens 102 at an area indicated by reticule 120 to access a corresponding area of the eye.

The method 200 may also comprise step 220 of removing contact lens 102 from the eye.

The contact lens body may be comprised of any suitable material, including those materials used in conventional contact lenses. After reading the disclosure herein, the skilled person will be readily able to select suitable materials including hydrogel polymers (e.g. hydroxyethylmethacrylate), silicone hydrogel polymers, rigid gas permeable polymers (e.g. silicone-acrylates, or fluoro-silicone-acrylates)

and hard lens polymers (e.g. polymethylmethacrylate), or a combination thereof. The figures show a number of embodiments of lenses with thickened regions to reduce lid pressure in the central zone of the lens.

Advantageously, the present invention does not require any complex or expensive equipment to accurately orient position relative to a patient's eye. A preferred advantage of the surgical guide and surgical method is that there is a reduced or no parallax error.

Advantageously, the contact lens will move with the eye, so any voluntary or involuntary motion of the patient will be inconsequential. If the contact lens does move relative to the eye, the contact lens should rapidly adopt the previous position without any difficulty, or can be repositioned by the surgeon.

Throughout the specification, the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

The invention claimed is:

1. A surgical guide comprising:
a conventional contact lens comprised of material used in a conventional contact lens and comprising a body, an external surface and an internal surface, wherein in position on an eye, the inner surface contacts the eye and the external surface is exposed, a reticule disposed on the body, whereby the reticule is used to guide a surgeon operating within the eye on which the contact lens is located;
whereby there is a reduced or no parallax error; and
wherein the contact lens will move with the eye and orient position relative to the eye to compensate for any voluntary or involuntary motion of the patient.

2. The surgical guide of claim 1, wherein the reticule is comprised on a surface of the contact lens.

3. The surgical guide of claim 1, wherein the reticule comprises one or more meridians.

4. The surgical guide of claim 1, wherein the reticule comprises one or more parallels.

5. The surgical guide of claim 1, wherein the reticule comprises a plurality of circles, squares, rectangles or any other shapes.

6. The surgical guide of claim 1, wherein the reticule comprises one or more duplex cross-hairs, wherein one or more bar of each of a respective duplex cross-hair is thick on the perimeter and thins out in the middle or in an area of interest.

7. The surgical guide of claim 1, wherein the reticule comprises two or more concentric shapes.

8. The surgical guide of claim 1, wherein the reticule comprises one or more region of different scale.

9. The surgical guide of claim 1, wherein the reticule is customised to an individual eye and wherein the reticule allows ready location of one or more target areas in the individual eye.

10. A surgical method, the method comprising:
using a reticule on a conventional contact lens comprised of material used in a conventional contact lens, the conventional lens comprising a body, an external surface and an inner surface, wherein in position on an eye, the inner surface contacts the eye and the external surface is exposed, the reticule disposed on the body, whereby the reticule is used to guide a surgeon operating on the eye on which the contact lens is located;
whereby there is a reduced or no parallax error;
wherein the contact lens will move with the eye and orient position relative to the eye to compensate for any voluntary or involuntary motion of the patient;
the conventional contact lens being used to guide a surgical procedure performed within the eye to thereby perform the surgical method.

11. The method of claim 10, further comprising the step of placing the contact lens onto the eye.

12. The method of claim 10, further comprising removing the contact lens.

13. The method of claim 10, wherein the reticule is comprised on a surface of the contact lens.

14. The method of claim 10, wherein the reticule comprises one or more meridians.

15. The method of claim 14, wherein the reticule comprises one or more parallels.

16. The method of claim 10, wherein the reticule comprises one or more duplex cross-hairs, wherein one or more bar of each of a respective duplex cross-hair is thick on the perimeter and thins out in the middle or in an area of interest.

17. The method of claim 10, wherein the reticule comprises two or more concentric shapes.

18. The method of claim 10, wherein the reticule comprises one or more region of different scale.

19. The method of claim 10, wherein a surgeon is operating within the eye.

20. The method of claim 10, wherein the conventional contact lens material comprises at least one of hydroxymethylmethacrylate, silicone hydrogel polymers, silicone-acrylates, fluoro-silicone-acrylates, and polymethylacrylate, or combinations thereof.

21. The surgical guide of claim 1, wherein the conventional contact lens material comprises at least one of hydroxymethylmethacrylate, silicone hydrogel polymers, silicone-acrylates, fluoro-silicone-acrylates, and polymethylacrylate, or combinations thereof.

22. The surgical guide of claim 1, wherein when the contact lens does move relative to the eye, the contact lens rapidly adopts the previous position without any difficulty, or can be repositioned by the surgeon.

23. The method of claim 10, wherein when the contact lens does move relative to the eye, the contact lens rapidly adopts the previous position without any difficulty, or can be repositioned by the surgeon.

* * * * *